United States Patent [19]

Sinclair et al.

[11] Patent Number: 4,732,861

[45] Date of Patent: Mar. 22, 1988

[54] METHOD AND APPARATUS FOR DETECTING OIL AEROSOL

[75] Inventors: Ian Sinclair; James I. T. Stenhouse, both of Loughborough, England

[73] Assignee: Domnick Hunter Filters Limited, Birtley, Great Britain

[21] Appl. No.: 920,834

[22] Filed: Oct. 17, 1986

[30] Foreign Application Priority Data

Oct. 18, 1985 [GB] United Kingdom ............... 8525774

[51] Int. Cl.$^4$ ............................................. G01N 25/30
[52] U.S. Cl. ..................................... 436/159; 422/94;
422/96; 422/97; 422/98; 436/139; 436/177
[58] Field of Search ................ 422/68, 94–98;
436/139, 155–159, 177

[56] References Cited

U.S. PATENT DOCUMENTS

| | | | |
|---|---|---|---|
| 3,460,909 | 8/1969 | Gayle | 422/97 |
| 4,057,721 | 11/1977 | de Vial et al. | 250/301 |
| 4,213,044 | 7/1980 | Perotta | 250/301 |
| 4,461,184 | 7/1984 | Gandhi | 73/863.25 |
| 4,563,246 | 1/1986 | Reed et al. | 422/209 |

Primary Examiner—Michael S. Marcus
Attorney, Agent, or Firm—Henry Sternberg; Bert J. Lewen

[57] ABSTRACT

A method of detecting oil aerosol in an air flow. The contaminated air is passed between an electrode (11) and an electrically conductive catalyst (14), and an electrical discharge therebetween causes electrostatic precipitation of oil on to the catalyst. Air flow and discharge are stopped, and the catalyst is heated with the air substantially stagnant until the catalytic combustion temperature of the oil is reached. The heat generation due to such combustion is sensed and used to produce an output signal indicative of the quantity of deposited oil.

12 Claims, 4 Drawing Figures

METHOD AND APPARATUS FOR DETECTING OIL AEROSOL

This invention relates to a method and apparatus for detecting oil aerosol in an air flow, for example a flow of compressed air from a compressor.

A conventional detection system for this purpose employs two balanced pellistors (pellistised resistors), one being a reference unit and the other being an active unit bearing a catalyst for hydrocarbon material. Palladium and platinum catalysts are, for example, known for this purpose. An air flow containing the oil aerosol passes over the two units and the combustible hydrocarbons are burnt on the active pellistor, the temperature increase caused by the catalytic oxidation being measured with a thermic bridge connected between the pellistors. The hydrocarbon vapour reaches the catalyst surface by steady state diffusion, and in order to allow the catalytic combustion to take place it is necessary to supply power to the pellistors to raise their temperature to a minimum activation temperature.

The present invention seeks to avoid the disadvantages of the conventional system and provide a reliable detection method.

According to a first aspect of the invention a method of detecting oil aerosol in an air flow comprises passing the air flow through a space between an electrode and an electrically conductive catalyst, causing electrical discharge between the electrode and the catalyst so as electrostatically to precipitate oil from the air flow on to the catalyst, terminating the discharge, stopping the air flow, heating the catalyst in substantially stagnant air to a temperature at which catalytic combustion of the precipitated oil occurs, and sensing heat generation due to said catalytic combustion to produce an output signal indicative thereof.

Heat generation increases as the quantity of precipitated oil increases, and the output signal is accordingly indicative of the quantity of oil in the air flow. The signal can thus be used to measure oil quantity, or to give a simple indication as to whether that quantity is abaove or below an acceptable level.

It will be seen that the method has two distinct phases. In the first phase the air flow passes between the electrodes, and oil aerosol from the flow is precipitated onto the catalyst. The amount of oil precipitated will depend on the concentration of oil aerosol in the air, on the rate of flow, on the spacing between the electrode and the catalyst, on the power of the discharge, and on the length of the period for which flow occurs. Precipitation efficiency has been found to reduce with increasing flow rate, and generally speaking it is preferred that the flow rate should not exceed 4 liters per minute, and desirably no more than two liters per minute. If only heavy contamination need be detected then the period of the first phase can be relatively brief, whereas if lighter contamination is to be detected a longer period is required in order to ensure that sufficient oil is precipitated on the catalyst for the second phase of the method to operate successfully. The spacing between the electrode and the catalyst may be different for different shapes of electrode. The spacing must not be too low, otherwise spark over will occur between the electrode and the catalyst, but it must be sufficiently low to ensure that a strong deposition field is present in the neighbourhood of the pellet. A suitable spacing will generally be from 10 mm to 50 mm, more preferably 15 mm to 30 mm. The electrode is desirably maintained at a negative potential relative to the catalyst; a suitable potential may be from 8 to 15 kV, with a value of around 10 and 12 kV being presently preferred.

In the second phase, the catalyst is heated to a temperature at which catalytic combustion commences, and this continues until all the precipitated oil has been burnt. The combustion causes significant heat generation, and the rise in temperature of the catalyst can be sensed and used to produce an output signal related to the heat output and thus to the quantity of deposited oil. The signal can then be interpreted as a measure of oil aerosol concentration in the air flow.

It is important that the catalytic combustion occurs in substantially stagnant air. If combustion occurs while there is any significant air flow it has been found that measurement of the generated heat can be distorted.

Preferably the oil is deposited on a pellistor coated with the catalyst, the pellistor is electrically heated to the catalytic combustion temperature, and heat generation is sensed by monitoring a variable of an electrical circuit in which the pellistor is included. This allows simple electrical heating and detection circuits to be used.

Preferably a second pellistor out of the air flow is heated during the period that air is flowing in order to stabilise an electrical heating circuit, and current from the stabilised circuit is switched from the second pellistor to the coated pellistor after the air flow has been stopped, in order to heat the coated pellistor.

It has been found that more reproducible results are obtained if the coated pellistor is brought rapidly to combustion temperature and the electrical heating circuit quickly stabilised accordingly. By employing a second pellistor element having substantially similar electronic characteristics to those of the coated pellistor, the circuit can be warmed up to a steady state, so that switching from the second pellistor to the coated pellistor after the circuit has been warmed up enables the required rapid heating and stabilisation to be obtained.

It has already been mentioned that it is important for the heating of the catalyst to be carried out in substantially stagnant air, and it is preferred that a predetermined delay is allowed to elapse between stopping the air flow and initiating heating of the catalyst, to ensure that the air is then reasonably still. A delay of about 30 seconds has been found suitable, and it is thought that a delay of between 15 and 45 seconds will be acceptable in practice.

Compressed air containing oil aerosol will very often also contain water aerosol, and when this is the case it is important that the method is capable of distinguishing between the two. During the precipitation phase, both oil and water will be precipitated on the catalyst, and as the catalyst is subsequently heated the evaporating water will tend to have a cooling effect that may tend to mask or distort the heating due to the catalytic combustion of the oil. It has been found that this difficulty may be overcome by heating the catalyst in two stages, an initial heating to a temperature sufficient to drive off water deposited on the catalyst and, after a predetermined cooling period, a further heating to the temperature at which catalytic combustion occurs. The effect of the initial heating is thus merely to drive off deposited water, and if the subsequent cooling period is sufficiently long it will ensure that the pellistor returns to a substantially reproducible and constant temperature irrespective of the amount of water that has been deposited and then evaporated. The further heating from this constant temperature will thus give a reproducible temperature rise to the temperature of catalytic combustion.

The invention also extends to an apparatus for detecting oil aerosol in an air flow, the apparatus comprising a vessel having inlet and outlet ports for the air flow, an electrode within the vessel, an electrically conductive catalyst within the vessel and spaced from the electrode to form a space through which the air flow passes, the catalyst being capable of causing catalytic combustion of oil, means for causing an electrical discharge between the electrode and the catalyst to cause electrostatic precipitation of oil on to the catalyst, means for heating the catalyst to a temperature at which catalytic combustion of the precipitated oil occurs, means for sensing heat generation due to said catalytic combustion to produce an output signal indicative thereof, and control means operative in sequence to commence said air flow, commence the electrical discharge, stop the electrical discharge, stop the air flow, commence heating of the catalyst and effect said sensing.

In order that the invention may be better understood a specific embodiment thereof will now be described in more detail, by way of example only, with reference to the accompanying drawings, in which.

Figure 1:
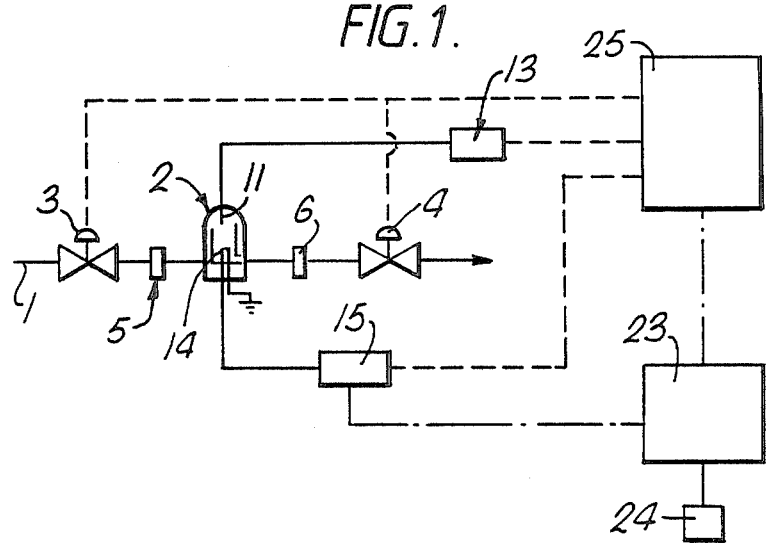
FIG. 1 is a schematic representation of the apparatus.

Referring to FIG. 1 this shows a compressed air line 1, that will generally be a measurement line connected in parallel to a main supply line. The line incorporates a standard compressed air line housing dome 2 having inlet and outlet ports to which the line is connected. A solenoid-operated input valve 3 and a solenoid-controlled regulator valve 4 are included in the line upstream and downstream of the housing respectively, and between each valve and the housing there is a flame arrestor 5, 6 respectively, that may in conventional manner be a suitably perforated copper gauze filter body.

Figure 2:
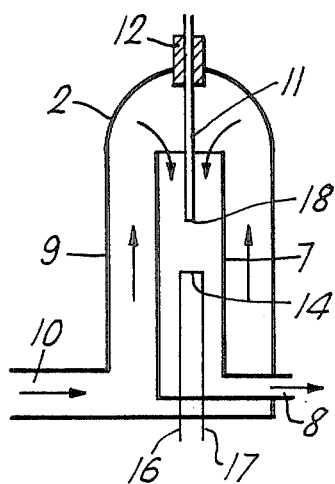
FIG. 2 is an enlarged view of the apparatus.

The housing arrangement is shown in more detail in FIG. 2, and it comprises a sleeve 7 defining an inner chamber and connected at 8 to an outlet, the sleeve being mounted within an outer member 9 connected to the inlet 10. The sleeve 7 terminates short of the top of the member 9. Air is thus constrained to flow in the direction of the arrows shown in FIG. 2. An electrode 11 of hard, electrically conductive metal, for example nickel molybdenum alloy, passes through an insulating sleeve 12 in the top of the housing and extends into the sleeve 7. The sleeve 12 may conveniently be of polytetrafluoroethylene, which as well as being electrically insulating also has chemically resistant properties. The electrode 11 is connected to a high tension unit 13 capable of maintaining the electrode at a negative potential of 8 to 15 kV, and preferably around 12 kV. Also located within the sleeve 7 is a pellistor 14 coated with catalyst on its surface, and electrically connected between a bridge circuit 15 and earth. The preferred catalyst is palladium, but platinum can alternatively be used and there may also be other suitable materials. The pellistor is supported on electrically conductive legs 16, 17 that should be sufficiently rigid to hold the pellistor substantially stationary as air flows through the sleeve 7. This may be achieved by suitable selection of materials, or by coating the legs with a hardenable adhesive material such as an epoxy resin.

The electrode 11 may be of any suitable form. In one arrangement the end 18 of the electrode is flat and may be positioned about 20 mm from the pellistor 14. Any spacing from 15 to 30 mm may be found suitable. In an alternative arrangement, the end 18 of the electrode may be pointed, and in this embodiment it is preferred that the end of the electrode lie substantially level with the upper end of the sleeve 7. The distance between the electrode and the pellistor may then be of the order of 40 mm.

Figure 3:
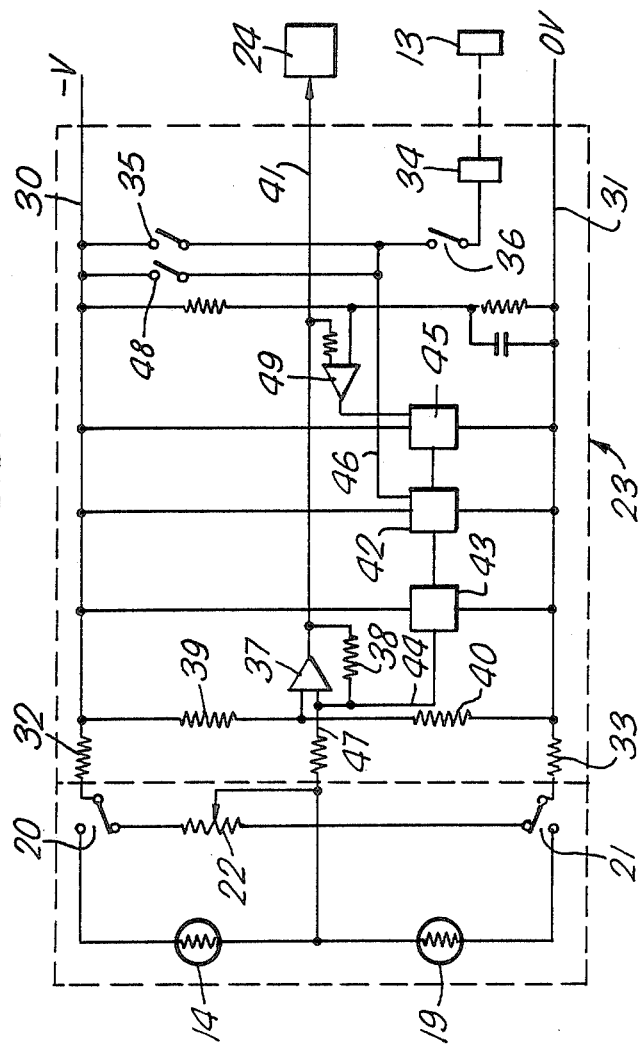
FIG. 3 is a schematic view of an electrical circuit embodied in the apparatus.

The bridge arrangement 15 is shown in more detail in FIG. 3, and it incorporates a second pellistor 19 that is included in a unit outside the housing and not affected by the air flow. The circuit includes switches 20 and 21 whereby either the coated pellistor 14 or the second pellistor 19 may be placed in the circuit and a variable resistor 22 which may be adjusted so that the electronic characteristics of the coated and second pellistors may be equalised with respect to the circuit.

The apparatus also includes an electrical circuit 23 connected to the bridge, a monitoring unit 24, and a timer unit 25 controlling the solenoids that operate the valves 3 and 4, controlling the high tension unit 13 and controlling the bridge network 15 and circuit 23.

The circuit 23 receives a smoothed and rectified current supply on rails 30 and 31, the supply being connected to the bridge network 15 through resistors 32,33. A relay 34 controls current supply to the high tension unit 13, the supply being present when switches 35 and 36 are closed to energise the relay. Switch 35 is a pressure-responsive switch located within the dome 2 and closed when the dome is pressurised. Switch 36 is operable by the timer to enable and disable the high tension supply.

An instrumentation amplifier 37 with a feedback loop 38 has one input connected across the supply rails 30,31 through resistors 39,40 of such value so as to hold the output on line 41 at approximately mid-rail value. A 12-bit binary counter 42 provides an output to a digital to analogue converter 43, the analogue section of which is configured to give a full scale output range between and including the power supply rails 30,31, and also continually to convert the output status of the counter 42 and supply a signal dependent thereon to a second input of amplifier 37 on line 44. An oscillator 45 drives the counter 43, which can be held in a metastable reset condition by supply on line 46 when the switch 35 or a further switch 48 is closed. The signal from the oscillator to the counter 45 can be inhibited by a comparator 49. The output from bridge network 15 is also applied to the second input to amplifier 37 on line 47 through an appropriate resistor. The output line 41 from the amplifier is connected to an appropriate instrument, for example an oscilloscope, and an alarm.

In use, the objective is to trace the voltage output from the coated pellistor 14 as a function of time, as the deposited oil burns off. For this to be useful, the starting point of the trace must be identical for every run, and the oscillator, counter and converter together form an auto-zeroing unit for the amplifier 37 which achieves this.

Operation will now be described. At the commencement of a test, the valves 3 and 4 are closed, switches 35,36 and 48 are open so that the high tension unit 13 is deenergised, and switches 20 and 21 are as shown in FIG. 3. The timer first controls opening of the valve 3, allowing air with any entrained oil and water aerosol to flow into the housing 2. The regulator valve 4 is then opened and controlled to achieve a steady flow state through the housing with the pressure within the housing being at any required value. It has been found advantageous to operate at pressures above atmospheric pressure, and a pressure of about 50 psig may be particularly suitable. A useful range is from 30 to 100 psig. Pressurisation of the dome causes switch 35 to close. Once steady flow has been established, the timer controls switch 36 to close and the high tension unit is thus switched on to apply a negative potential of about $-12$ kV to the electrode 11. Corona discharge occurs between the electrode and the pellistor 14, whereupon oil and water particles entrained in the air take on a negative charge and migrate to the coated pellistor 14 to be precipitated thereon. The negative potential is maintained for any required preset period, which period depends on the expected oil concentration. A typical period for those levels of contamination usually found is about 30 minutes, but this may be extended to several hours in conditions of very low contamination.

Towards the end of the flow period the timer operates switch 21 and power is thus supplied to the second pellistor 19, which is chosen to have substantially the same electronic characteristics as the coated pellistor 14. Any small variation between the characteristics can be compensated for by adjustments of the resistor 22. This supply allows the electronic heating circuit to warm up to a steady state, which should be achieved by the end of the flow period.

After closing the valves 3 and 4, a delay of about 30 seconds is allowed, during which time air movement within the dome substantially ceases. Switch 21 is then opened and switch 20 closed to switch the power from the second to the coated pellistor, so heating this to drive off water that has been precipitated thereon. During this period (typically about one second) the pellistor temperature does not reach a sufficiently high level to cause catalytic combustion of the deposited oil. After the initial heating period the heating circuit is again switched back to the second pellistor and the coated pellistor 14 is allowed to cool over a further period of about 30 seconds. At the end of the cooling period, the heating circuit is re-connected to the coated pellistor to raise the temperature to the catalytic combustion temperature, typically reached in about two seconds, whereupon the deposited oil burns off the catalyst, causing a significant increase in the temperature of the pellistor.

While switch 35 is closed the counter 42 is held in its reset condition, and as a result thereof the analogue output of converter 43 is held close to zero volts and the output of the amplifier 37 on line 41 is forced to approach that of rail 30. When the valves 3 and 4 are closed the pressure within the dome falls, and switch 35 opens, so switching off the high tension unit 13. Opening of switch 35 also removes the reset voltage from the counter 42, as a result of which the counter commences to count the signals from the oscillator 45. The digital signal from the counter is passed to the converter 43 which produces a reference signal to the amplifier to alter the offset current thereto. The comparator monitors the output of the amplifier and when this reaches a preset value it controls the oscillator 45 to disable the clock output to the counter 42. The result of this is that the bridge is balanced very quickly after depressurisation of the sensor head, so providing an output of constant known value on line 41 at the beginning of each test.

Figure 4:
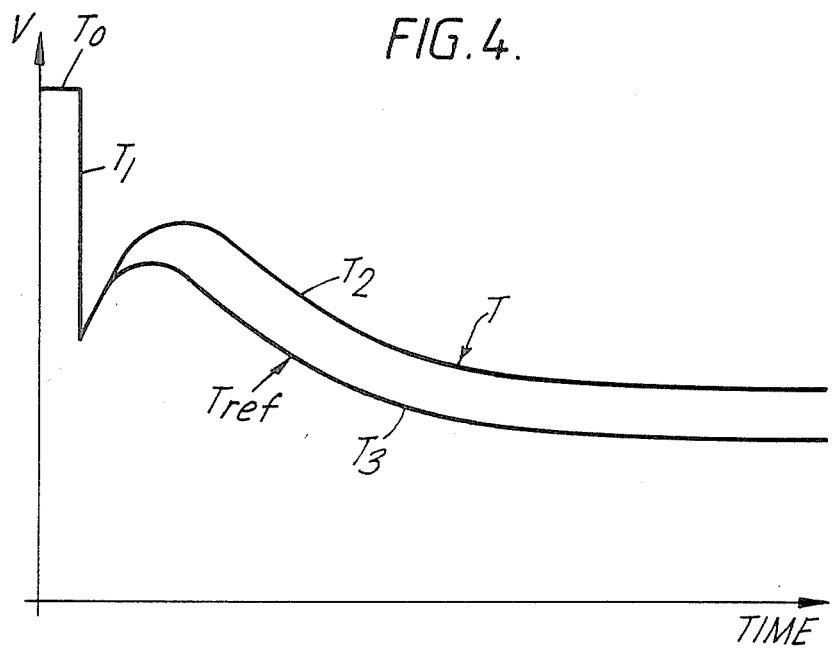
FIG. 4 shows typical output signals from the apparatus.

As the oil burns off the pellistor 14 the additional heat released will quickly increase the voltage output supplied to the amplifier 37 on line 47, causing a corresponding rise in the votage on line 41 to the monitoring unit 24, typically an oscilloscope. A typical oscilloscope trace T from line 41 shown in FIG. 4; section $T_0$ is the top rail voltage, section $T_1$ shows the effect of auto-zeroing and section $T_2$ the effect of heating the pellistor to catalytic combustion temperature and subsequent combustion of the deposited oil.

To arrive at a value for oil contamination the derived signal must be compared with a reference signal, and it is preferred to generate such reference signal after combustion has been completed, so that the pellistor 14 is then in its clean condition. Accordingly, following complete combustion, the timer operates to switch power back to the second pellistor 19 from the coated pellistor 14, so allowing this to cool, switch 36 is opened to disable the high tension unit 13, switch is closed 48 so resetting the counter to force the amplifier output to top rail value and is then opened so that the auto-zeroing process is effected, and power is then switched back to the coated pellistor 14 to bring this back to catalytic combustion temperature. The typical oscilloscope trace from line 41 is shown as $T_{ref}$, and it will be noted that sections $T_0$ and $T_1$ are identical to those of trace T, but that section $T_3$ is lower than section $T_2$ of trace T. The difference is a measure of the heat of combustion and thus of the quantity of oil. The voltage signal of the two traces can be integrated to give digital values representative thereof, and the two values can be compared.

If the difference between the two values is sufficient to indicate that a quantity of oil above a given minimum value has been burnt then a signal indicative of this is produced, which can activate an alarm circuit showing that contamination of the air flow is at an unacceptable level. If the amount of oil deposited and therefore burnt off is at or below the acceptable minimum then the difference between the two signals will not be sufficient to activate the alarm circuit.

We claim:

1. A method of detecting oil aerosol in an air flow, the method comprising passing the air flow through a space between an electrode and an electrically conductive catalyst, causing electrical discharge between the electrode and the catalyst so as electrostatically to precipitate oil from the air flow on to the catalyst, terminating the discharge, stopping the air flow, heating the catalyst in substantially stagnant air, to a temperature at which catalytic combustion of the precipitated oil occurs, and sensing heat generation due to said catalytic combustion to produce an output signal indicative thereof.

2. A method according to claim 1 in which the flow rate of air between the electrode and the catalyst is not greater than 4 liters per minute.

3. A method according to claim 1 in which the flow rate of air between the electrode and the catalyst is not greater than 2 liters per minute.

4. A method according to claim 1 in which the electrode is maintained at a negative potential of from 8 to 15 kV with respect to the catalyst.

5. A method according to claim 1 in which the oil is deposited on a pellistor coated with the catalyst, the pellistor is electrically heated to the said temperature, and heat generation is sensed by monitoring a variable of an electrical circuit in which the pellistor is included.

6. A method according to claim 5 in which, during the period of air flow, an electrical heating circuit heats a second pellistor located out of the air flow, the second pellistor having electronic characteristics substantially similar to those of the coated pellistor, in order to stabilise the circuit, and current from the stabilised circuit is switched from the second pellistor to the coated pellistor after the air flow has been stopped, in order to heat the coated pellistor.

7. A method according to claim 1 in which a delay of from 15 to 45 seconds is allowed to elapse between stopping the air flow and initiating heating of the catalyst.

8. A method according to claim 1 in which the catalyst is heated in two stages, an initial heating stage to a temperature sufficiently high to drive off water deposited on the catalyst and, after a predetermined cooling period, a further heating stage to a higher temperature at which catalytic combustion occurs.

9. Apparatus for detecting oil aerosol in an air flow, the apparatus comprising a vessel having inlet and outlet ports for the air flow, an electrode within the vessel, an electrically conductive catalyst within the vessel and spaced from the electrode to form a space through which the air flow passes, the catalyst being capable of causing catalytic combustion of oil, means for causing an electrical discharge between the electrode and the catalyst to cause electrostatic precipitation of oil on to the catalyst, means for heating the catalyst to a temperature at which catalytic combustion of the precipitated oil occurs, means for sensing heat generation due to said catalytic combustion to produce an output signal indicative thereof, and control means operative in sequence to commence said air flow, commence the electrical discharge, stop the elctrical discharge, stop the air flow, commence heating of the catalyst and effect said sensing.

10. Apparatus according to claim 9 in which means are provided for maintaining the electrode at a negative potential of from 8 to 15 kV with respect to the catalyst.

11. Apparatus according to claim 9 and claim 10 in which the catalyst is coated on to a pellistor, an electrical heating circuit is connected to the pellistor for heating the catalyst, and, monitoring means are provided for monitoring a variable of the circuit.

12. Apparatus according to claim 11 and including a second pellistor having electronic characteristics substantially similar to that of the coated pellistor, and means for switching the heating circuit to cause heating of either the coated pellistor or the second pellistor.

* * * * *